(12) United States Patent
Janda et al.

(10) Patent No.: US 6,642,035 B2
(45) Date of Patent: Nov. 4, 2003

(54) SYNTHESIS OF B-KETO ESTERS

(75) Inventors: Kim D. Janda, La Jolla, CA (US); Armando Cordova, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 09/771,475

(22) Filed: Jan. 26, 2001

(65) Prior Publication Data

US 2002/0102671 A1 Aug. 1, 2002

(51) Int. Cl.[7] .............................. C12P 7/62; C12P 1/00; C12P 37/00
(52) U.S. Cl. .......................... 435/135; 435/41; 435/43
(58) Field of Search ............................ 435/41, 43, 135

(56) References Cited

U.S. PATENT DOCUMENTS 5,817,490 A * 10/1998 Hubbs
6,365,398 B1 * 4/2002 Bornscheuer et al.

OTHER PUBLICATIONS

Oikawa, et al., "Meldrum's Acid in Organic Synthesis. 2. A General and Versatile Synthesis of β–Keto Esters", *J. Org. Chem. 43*: 2087–2088 (1978).

Taber, et al., "Preparation of β–Keto Esters by 4–DMAP–Catalyzed Ester Exchange", *J. Org. Chem. 50*: 3618–3619 (1985).

Gilbert, et al., "Transesterification of 3–Oxo Esters with Allylic Alcohols", *J. Org. Chem. 53*: 449–450 (1988).

Hudlicky, et al., "Yeast–Mediated Resolution of β–Keto Esters of Prochiral Alcohols", *J. Org. Chem. 56*: 3619–3623 (1991).

Faber, et al., "Enzyme–Catalyzed Irreversible Acyl Transfer", *Synthesis*: 895–910 (1992).

Landias, et al., "Asymmetric Metal Carbene Insertion into the Si–H Bond", *Tet. Lett. 35*: 4565–4568 (1994).

Jeromin, et al., "Diketene a New Esterification Reagent in the Enzyme–Aided Synthesis of Chiral Alcohols and Chiral Acetoacetic Acid Esters", *Tet. Lett. 36*: 6663–6664 (1995).

Suginaka, et al., "Highly Selective Resolution of Secondary Alcohols and Acetoacetates with Lipases and Diketene in Organic Media", *Tetrahedron: Asymmetry 7*: 1153–1158 (1996).

Balaji, et al., "A Facile and Selective Synthesis of β–Keto Esters via Zeolite Catalysed Transesterification", *J. Chem. Soc., Chem. Commun.*: 707–708 (1996).

Mottet, et al., "A Simple and Efficient Preparation of Propargylic β–Keto Esters through Transesterification", *J. Org. Chem. 64*: 1380–1382 (1999).

* cited by examiner

*Primary Examiner*—Jon P. Weber
*Assistant Examiner*—Kailash C. Srivastava
(74) *Attorney, Agent, or Firm*—Donald G. Lewis

(57) ABSTRACT

β-keto esters are prepared by way of a lipase-catalyzed transesterification. The synthetic methodology provides a simple scheme for the synthesis of optically active β-keto esters that are useful building blocks and starting materials for natural product synthesis. Moreover, the methodology employs mild, solvent-free conditions. The methodology may also be employed for resolving racemic alcohols.

6 Claims, 3 Drawing Sheets

| Entry | Alcohol | β-keto ester | Product | % Yield |
|---|---|---|---|---|
| 1 | Ph-CH=CH-CH2OH (1) | RO-C(O)-CH2-C(O)-CH3 (13) | Ph-CH=CH-CH2-O-C(O)-CH2-C(O)-CH3 (17) | 95 |
| 2 | (CH3)2C=CH-CH2OH (2) | 13 | prenyl acetoacetate (18) | 95 |
| 3 | cis-pent-2-enol (3) | 13 | (19) | 98 |
| 4 | pent-2-ynol (4) | 13 | (20) | 92 |
| 5 | BnOH (5) | 13 | benzyl acetoacetate (21) | 94 |
| 6 | Me(OCH2CH2)nOH (6) | 13 | (22) | 97 |
| 7 | PhCH2CH2CH(OH)CH=CH2 (7) | 13 | (23) | 95 |
| 8 | HO-C6H4-CH2CH2CH(OH)CH3 (8) | 13 | (24) | 95 |
| 9 | 1 | RO-C(O)-CH2-C(O)-CH2CH2Ph (14) | (25) | 92 |
| 10 | 4 | 14 | (26) | 93 |
| 11 | 1 | RO-C(O)-CH2-C(O)-CH=CH2 (15) | (27) | 94 |
| 12 | 5 | 2-oxocyclopentanecarboxylate (16) | (28) | 92 |

Figure 2

| Entry | Substrate | Products | | | % Conv. | %ee$_s$ (yield) | % ee$_p$ (yield) | E |
|---|---|---|---|---|---|---|---|---|
| 1 |  29 |  (S) - 29 |  (R) - 32 | | 51 | 98 (45) | 96 (41) | 226 |
| 2 |  7 |  (R) - 7 |  (S) - 23 | | 51 | 96 (44) | 92 (42) | 70 |
| 3 |  30 |  (S) - 30 |  (R) - 33 | | 48 | 90 (38) | 97 (41) | 203 |
| 4 |  31 |  (S) - 31 |  (R) - 34 | | 51 | 96 (46) | 93 (40) | 103 |

SYNTHESIS OF B-KETO ESTERS

FIELD OF THE INVENTION

The invention relates to the synthesis of β-keto esters. More particularly, the invention relates to a highly chemo- and stereoselective synthesis of β-keto esters via a polymer-supported lipase catalyzed transesterfication.

BACKGROUND

β-keto esters are noteworthy in that they represent an important class of organic building blocks used in the synthesis of complex natural products (S. Benetti, et al., *Chem Rev.* 1995, 95, 1065). A seemingly straight-forward method to prepare these molecules is through an alcohol based transesterification (J. G. Gilbert, et al., *J. Org. Chem.* 1988, 53, 449; D. F. Taber, et al., *J. Org. Chem.* 1985, 50, 3618). Yet the synthesis of allylic and propargylic β-keto esters is not trivial by this route due to their acid/base lability and sigmatropic rearrangement of the β-keto ester. To circumvent these problems a report has appeared describing the heating of alcohols with β-keto esters in toluene (C. Mottet, et al., *J. Org. Chem.* 1999, 64, 138;). However, the reaction times were lengthy and yields variable for many of the substrates. Another mild method uses crystalline microporous nanosilicates (zeolites) as the catalyst for the transesterification in refluxing toluene to avoid potential side reactions, but here the yields were even lower compared to the former case (B. S. Balaji, et al., *J. Chem. Soc. Chem. Commun.* 1996, 707). Furthermore, none of these or any of the conventional methods display stereoselectivity or chemoselectivity between aliphatic alcohols or phenols. What is required is a general method of synthesizing β-ketoesters either as racemates or as single enantiomers. What is required is a general method for resolving alcohol racemates.

SUMMARY OF INVENTION

*Candida antarctica* lipase B (CALB) immobilized on a macroporous poly(propylene) resin (Novozym 435) catalyzed the transesterification of β-keto esters under environmentally safe conditions. The reactions were performed by simply solubilizing the alcohols in methyl or ethyl β-keto esters and then treating the reaction mixture with the lipase under reduced pressure. The β-keto ester products were obtained in high yields (>90%) and CALB was chemoselective in the acylation of aliphatic alcohols in the presence of phenols. In addition, CALB was able to resolve sec-alcohols with high enantioselectivity. This is a general route to prepare β-keto esters by lipase-catalyzed transesterification and it can be of ample use due to its mild, solvent-free conditions. Moreover, it also provides a simple protocol to produce optically active β-keto esters that are useful building blocks and starting materials for natural product synthesis.

One aspect of the invention is directed to a process for synthesizing chiral β-keto ester products by way of a lipase catalyzed transesterification. In the first step of the process, an acyl donor β-keto ester, a racemic alcohol, and a catalytic concentration of a lipase are admixed under catalytic contitions. In the second step of this aspect of the invention, a transesterification of the acyl donor β-keto ester with the racemic alcohol is catalyzed by means of the lipase for producing the chiral β-keto ester product. Preferred racemic alcohols include allylic, propargylic, benzylic, allenic, and aliphatic alcohols. A preferred lipase is *Candida antartica* lipase B (CALB). Preferred acyl donor β-keto esters include a methyl ester or an ethyl ester. A preferred solvent is the acyl donor β-keto ester.

Another aspect of the invention is directed to a process for resolving a racemic alcohol. In the first step of the process the racemic alcohol is admixed with a catalytic concentration of a lipase in the presence of an excess of acyl donor β-keto ester under catalytic contitions. In the second step of the process, a transesterification of the acyl donor β-keto ester with the racemic alcohol is catalyzed by means of lipase for resolving the racemic alcohol. producing the chiral β-keto ester product. Preferred racemic alcohols include allylic, propargylic, benzylic, allenic, and aliphatic alcohols. A preferred lipase is *Candida antartica* lipase B (CALB). Preferred acyl donor β-keto esters include a methyl ester or an ethyl ester. A preferred solvent is the acyl donor β-keto ester.

BRIEF DESCRIPTION OF DRAWINGS

FIG. 2 illustrates a table disclosing a range of substrates, products and yields obtained in the transesterification reaction.

DETAILED DESCRIPTION

Lipases are a class of serine hydrolases that can exhibit excellent stereoselectivity and good catalytic activity for transesterification reactions in organic solvents (C. H. Wong, et al., *Enzymes in synthetic organic chemistry;* Tetrahedron Organic Chemistry Series Vol. 12.; Baldwin, J. E., Ed.; Pergamon Press: New York, 1994; K. Faber, *Biotransformations in Organic Chemistry. A Textbook,* 2nd ed; Springer-Verlag: New York, 1995). It is disclosed herein that lipases may be employed for the preparation of chiral β-keto esters. Indeed, using diketene as the acyl donor, the synthesis of chiral acetoacetate esters by lipase catalysis was recently reported (K. Suginaka, et al., *Tetrahedron: Asymmetry* 1996, 4, 1153). While this study was informative it was narrow in scope. Expansion on this theme using methyl or ethyl β-keto esters as the acyl donors would give a broader range of compounds. Furthermore, these structures could be synthesized in combination with the kinetic resolution of secondary alcohols so as to achieve a direct route to chiral β-keto esters. Disclosed herein is a general method that avoids the use of bulk solvent wherein a range of alcohols were reacted with methyl or ethyl β-keto esters to obtain the desired transesterified products in excellent yield and with high chemo- and stereoselectivity.

Figure 1:
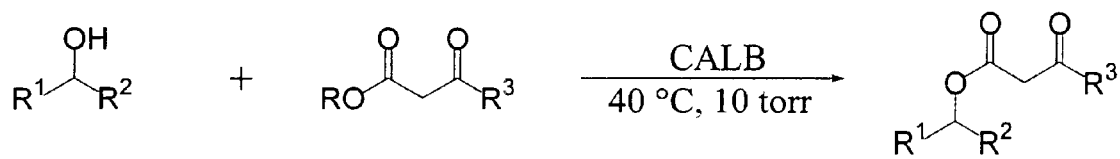
FIG. 1 illustrates a transesterification reaction catalyzed by *Candida antarctica* Lipase B.

The catalyst employed was *Candida antarctica* lipase B (CALB) immobilized on a macroporous resin. An immobilized lipase was used as it enables ease of handling and recovery of the catalyst (FIG. 1). The simplicity of the method is demonstrated in the following typical example. A homogeneous mixture of alcohol (5 mmol) and β-keto ester (40 mmol) was treated with 10% (w/w of alcohol) of the catalyst and swirled in a flask connected to Büchi rotavapor at 40° C. and 10 torr. Under these conditions the liberated EtOH or MeOH, known inhibitors of lipases, are removed by evaporation. After 8 hours, the reaction mixture was filtered, rinsed ($CH_2Cl_2$), concentrated and purified by chromatography to yield the desired product (FIG. 2). The immobilized lipase could be reused without loss of activity by first washing the beads with $CH_2Cl_2$ and then drying them in a desiccator. Because a one-pot operation was used, the procedure was further generalized such that reactions were also performed in parallel by the use of a vaccum oven. Furthermore, this strategy could be used to create a lipase-catalyzed β-keto ester library. In virtually all cases that have been investigated, excellent results were obtained, generally superior to those found in the literature (supra).

Both primary and secondary alcohols were appropiate substrates for the lipase as were allylic and propargylic alcohols. Interestingly, the lipase also efficiently acylated the polymer poly(ethylene glycol) monomethyl ether (MeO-PEG$_{5000}$) (Entry 6). The ability of CALB to use MeO-PEG$_{5000}$ as a substrate is noteworthy in that it can provide a variety of β-keto ester terminated PEGs that could be used as starting points in a polymer supported synthesis of heterocycles (M. F. Gordeev, et al., *Tetrahedron Lett.* 1996, 37, 4643). Using 8, chemoselectivity between a phenol and alcohol was examined. The exclusive formation of 24 elucidates CALB's chemoselectivity for alkyl alcohols compared to phenols. CALB was also able to utilize the well known annelating reagent ethyl 3-oxo-4-pentenoate (15, Nazarov's reagent) as an acyl donor to form 27 in excellent yield (Entry 11) (I. N. Nazarov, et al., *Zh. Obshch. Khim.* 1953, 23, 1703.; *Engl. Transl.* 1953, 23, 1793). This procedure could be applied for the one-step preparation of various annelating agents (3-oxo-4-pentenoate esters), since they do not have to be individually prepared from the corresponding acetate ester (two steps) (R. Zibuck, et al., *J. Org. Chem,* 1989, 54, 4717). Furthermore, it should be noted that attempts to prepare 27 by conventional methods using the 5-acyl derivative of Meldrum's acid were unsuccesful (Y. Oikawa, et al., *J. Org. Chem.* 1978, 43, 2087).

Figure 3:
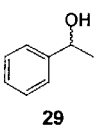
FIG. 3 illustrates a table disclosing the yield and enantiomeric purity of products obtained by kinetic resolution of secondary alcohols using *Candida antarctica* Lipase B.
Figure 3:
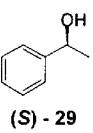
Figure 3:
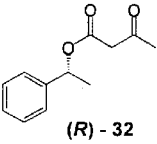
Figure 3:
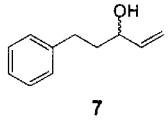
Figure 3:
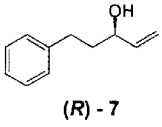
Figure 3:
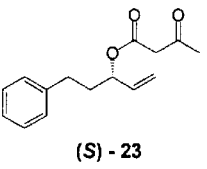
Figure 3:
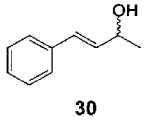
Figure 3:
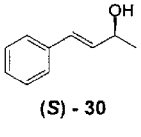
Figure 3:
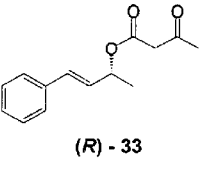
Figure 3:
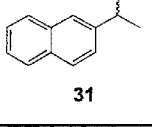
Figure 3:
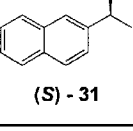
Figure 3:
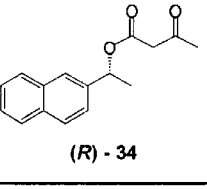

To investigate CALB's ability to resolve racemic secondary alcohols, reactions were run with mixtures of the alcohol (5 mmol) and β-keto ester (7.5 mmol) to which 10% (w/w of alcohol) of the catalyst was added. After 1.5 hours (~50% conversion of the alcohol) the reaction was stopped by filtration of the immobilized lipase and worked up in a similar manner as detailed (vide supra). CALB displayed good E values (E=enantiomeric ratio: Chen, C. - S.; Y. Fujimoto, et al., *J. Am. Chem. Soc.* 1982, 104, 7294) for all of the tested alcohols and the ee values were above 90% (FIG. 3). The successful formation of (R)-33, demonstrates that the method could be a direct starting point for transfer of chirality in nonracemic cyclic and acyclic systems (R. K. Hill, *Asymmetric Synthesis;* Vol. 3; Academic Press; Orlando. 1984, p. 503; F. E. Ziegler, *Chem. Rev.* 1988, 88, 1423; M. Tanabe, et al., *J. Am. Chem. Soc.* 1980, 102, 862). Furthermore, this protocol presents an additional advantage to previous methods utilizing diketene as the acyl donor for the lipase, since it can accommodate a greater variety of acyl donors (i. e. β-keto esters) (G. Jeromin, et al., *Tetrahedron Lett.* 1996, 37, 6663).

EXAMPLES

General Methods: Methyl and ethyl acetoacetate were obtained from Aldrich Chemical Co. and distilled prior to use. β-ketoester 22 and Nazarov's reagent 24 were synthesized according to literature procedures (I. N. Nazarov, et al., *Zh. Obshch. Khim.* 1953, 23, 1703.; *Engl. Transl.* 1953, 23, 1793; L. Weiler, *J. Am. Chem. Soc.* 1970, 92, 6707). Chiral HPLC analyses were carried out using a Daicel Chiralcel OD Column (250 mm, 4.6 mm, eluent: hexane/2-Propanol). Column chromatography purification was done using Merck 60 silica gel (particle size 0.04–0.063 mm). The lipase (component B) Novozym 435 derived from *Candida antarctica* is is a product of Novo Nordisk A/S Denmark. The enzyme used was an immobilized preparation on a macroporous poly(propylene) resin, containing 1% (w/w) enzyme, with a catalytic activity of approximately 25 000 LU/g preparation. CALB was dried in a desiccator over $P_2O_5$ prior to use. All glassware was oven dried prior to use.

Lipase-Catalyzed Transesterifications: A homogenous mixture of alcohol (5 mmol) and β-ketoester (20 mmol) was treated with 10% (w/w of alcohol) of the catalyst and swirled in a 50-mL flask connected to a Büchi rotavapor at 40° C. and 10 torr. For entries 9–12 (FIG. 2), the ratio was 1.2 to 1 between alcohol and β-ketoester, respectively. After 8 hours, 20 mL of $CH_2Cl_2$ was added and the polymer-supported lipase removed by filtration. The solvent was removed under reduced pressure and the crude product purified by silica-gel column chromatography with increasing amounts of EtOAc in hexane. The spectral data for 17, 18, 19 and 21 were in accordance with those reported in literature (J. G. Gilbert, et al., *J. Org. Chem.* 1988, 53, 449; D. F. Taber, et al., *J. Org. Chem.* 1985, 50, 3618; C. Mottet, et al., *J. Org. Chem.* 1999, 64, 138; B. S. Balaji, et al., *J. Chem. Soc. Chem. Commun.* 1996, 707; M. P. Doyle, et al., *J. Am. Chem. Soc.* 1995, 117, 5763.).

Lipase Catalyzed Parallel Reactions: Vials containing different mixtures of alcohols (1 mmol) and β-ketoesters (8 mmol) together with 10 mg of CALB were placed in a vaccum oven at 40° C. and 10 torr. After 24 hours, 3 mL of $CH_2Cl_2$ was added to each vial and the lipase filtered. The work-up was performed as described (vide supra).

Lipase-Catalyzed Kinetic Resolutions: The reactions were performed as described for the lipase-catalyzed transesterifications (vide supra), however now with a ratio of 3:2 between β-ketoester and alcohol and reacted for 1.5 hours (~50% conversion). Due to solubility problems, the ratio was 4:1 for alcohol 31. The spectral data for (R)-32 and (R)-34 were in accordance with those reported in literature (K. Suginaka, et al., *Tetrahedron: Asymmetry* 1996, 4, 1153).

MeO-PEG-3-Oxobutanoate (22): Poly(ethyleneglycol) monomethyl ether ($M_w$ 5000) (5.0 g, 1 mmol) was dissolved in methyl acetoacetate (10 mL, 80 mmol) and reacted with CALB (500 mg) according to the general transesterification procedure. After 8 hours the reaction mixture was dissolved in THF (50 mL), filtered, and precipitated into diethyl ether (800 mL) at 0° C. The white precipitate was collected to afford the product as a white solid (4.98 g, 97%).

Ethenyl-3-phenylpropyl 3-oxobutanoate (S)-(23): $[\alpha]^{25}_D$=3.7((c=2.1, $CH_2Cl_2$), 90% ee; Chromatography: EtOAc:hexane-10:90 (20:80).

Methyl 3-(4-hydroxyphenyl)propyl 3-oxobutanoate (24): Chromatography: EtOAc:hexane-10:90 (50:50).

Cinnamyl-3-oxo-5-phenylpentanoate (25): Chromatography: EtOAc:hexane-20:80(10:30).

Cinnamyl-3-oxo-4-pentenoate (27): Chromatography: EtOAc:hexane-20:80(10:30).

Benzyl 2-oxocyclopentanecarboxylate (28): Chromatography: EtOAc:hexane-10:90 (20:80).

Methyl-3-phenylprop-2-enyl 3-oxobutanoate ((R)-33): $[\alpha]^{25}_D$=+81.1((c=1.1, $CH_2Cl_2$), 93% ee; Chromatography: EtOAc:hexane-10:90 (40:60).

What is claimed is:

1. A process for synthesizing a chiral β-keto ester product, the process comprising the following steps:

Step A: admixing an acyl donor β-keto ester and a racemic alcohol with a catalytic concentration of a lipase under catalytic contitions; and then Step B: catalyzing transesterification of the acyl donor β-keto ester with the racemic alcohol by means of the lipase to produce the chiral β-keto ester product.

2. A process as described in claim 1, wherein the racemic alcohol is selected from the group consisting of allylic, propargylic, benzylic, allenic, and aliphatic alcohols.

3. A process as described in claim 2, wherein the lipase is *Candida antarctica* lipase B.

4. A process as described in claim 1, wherein the acyl donor β-keto ester is a methyl ester.

5. A process as described in claim 1, wherein the acyl donor β-keto ester is an ethyl ester.

6. A process as described in claim 2, wherein the acyl donor β-keto ester serves as a solvent.

* * * * *